(12) United States Patent
Bogdan et al.

(10) Patent No.: US 8,071,831 B1
(45) Date of Patent: Dec. 6, 2011

(54) PROCESS FOR XYLENE AND ETHYLBENZENE ISOMERIZATION USING UZM-35

(75) Inventors: Paula L. Bogdan, Mount Prospect, IL (US); Deng-Yang Jan, Elk Grove Village, IL (US); Christopher P. Nicholas, Evanston, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 18 days.

(21) Appl. No.: 12/820,088

(22) Filed: Jun. 21, 2010

(51) Int. Cl.
*C07C 5/27* (2006.01)
(52) U.S. Cl. ...................................... 585/481
(58) Field of Classification Search ................... 585/481
See application file for complete search history.

(56) References Cited

U.S. PATENT DOCUMENTS

| | | | |
|---|---|---|---|
| 2,620,314 A | 12/1952 | Hoekstra | |
| 3,201,491 A | 8/1965 | Stine et al. | |
| 3,626,020 A | 12/1971 | Neuzil | |
| 3,696,107 A | 10/1972 | Neuzil | |
| 4,039,599 A | 8/1977 | Gewartowski | |
| 4,184,943 A | 1/1980 | Anderson | |
| 4,381,419 A | 4/1983 | Wylie | |
| 4,402,832 A | 9/1983 | Gerhold | |
| 4,440,871 A * | 4/1984 | Lok et al. | 502/214 |
| 4,910,006 A | 3/1990 | Zones et al. | |
| 4,957,891 A | 9/1990 | Sachtler et al. | |
| 4,963,337 A | 10/1990 | Zones | |
| 5,512,267 A | 4/1996 | Davis et al. | |
| 6,048,449 A | 4/2000 | Bogdan et al. | |
| 6,049,018 A | 4/2000 | Calabro et al. | |
| 6,143,941 A | 11/2000 | Sharma et al. | |
| 6,776,975 B2 | 8/2004 | Wilson et al. | |
| 7,525,008 B2 | 4/2009 | Bogdan et al. | |
| 7,578,993 B2 | 8/2009 | Lewis et al. | |
| 7,922,997 B2 | 4/2011 | Moscoso et al. | |
| 2009/0318696 A1 | 12/2009 | Strohmaier et al. | |

OTHER PUBLICATIONS

Lobo, CIT-1: A New Molecular Sieve with Intersecting Pores Bounded by 10- and 12-Rings, Journal of American Chemical Society, 1995, pp. 3766-3779, vol. 117.
Wright, Synthesis and Structure of Novel Large-pore Microporous Magnesium-containing Aluminophosphate, Journal of the Chemical Society, Chemical Communications, 1993, pp. 633-635, Issue 7.
Muncaster, An in Situ Microcrystal X-ray Diffraction Study of the Synthetic Aluminophosphate Zeotypes DAF-1 and CoAPSO-44, Chemistry of Materials, 1999, pp. 158-163, vol. 11.

\* cited by examiner

*Primary Examiner* — Thuan Dinih Dang
(74) *Attorney, Agent, or Firm* — Maryann Maas

(57) ABSTRACT

Xylene and ethylbenzene isomerization process is catalyzed by the UZM-35 family of crystalline aluminosilicate zeolitic compositions represented by the empirical formula:

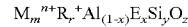

$$M_m^{n+}R_r^+Al_{(1-x)}E_xSi_yO_z$$

where M represents a combination of potassium and sodium exchangeable cations, R is a singly charged organoammonium cation such as the dimethyldipropylammonium cation and E is a framework element such as gallium. These UZM-35 zeolitic compositions are active and selective in the isomerization of xylenes and ethylbenzene.

20 Claims, 4 Drawing Sheets

US 8,071,831 B1

PROCESS FOR XYLENE AND ETHYLBENZENE ISOMERIZATION USING UZM-35

FIELD OF THE INVENTION

The present invention relates to the use of zeolitic UZM-35 composition in a process of isomerizing xylenes and ethylbenzene. The zeolitic UZM-35 composition may be present in the catalyst as unmodified zeolitic UZM-35 composition or as modified zeolitic UZM-35 composition. The UZM-35 containing catalyst may take one of several forms, including for example a spherical oil-dropped catalyst or an extruded catalyst.

BACKGROUND OF THE INVENTION

Zeolites are crystalline aluminosilicate compositions which are microporous and which have a three-dimensional oxide framework formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Topological zeolite structures are described in *Atlas of Zeolite Framework Types*, which is maintained by the International Zeolite Association Structure Commission at http://www.iza-structure.org/databases/. Zeolites can be used as catalysts for hydrocarbon conversion reactions, which can take place on outside surfaces as well as on internal surfaces within the pore.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieve ethylbenzene isomerization to xylenes with high conversion, would effect significant improvements in xylene-production economics.

Especially advantageous would be a commercially utilizable catalyst containing 12-membered rings and 10-membered rings in the same 3-dimensional structure. Commercial utility is typically seen in aluminosilicate structures which are synthesized in hydroxide media with readily available structure directing agents. Zeolites which contain both 12-membered and 10-membered rings in 3-dimensional structures belong to the CON, DFO, IWR, IWW and MSE structure types. The synthesis of CIT-1, a zeolite of the CON structure type, is described in U.S. Pat. No. 5,512,267 and in J. Am. Chem. Soc. 1995, 117, 3766-79 as a borosilicate form. After synthesis, a subsequent step can be undertaken to allow substitution of Al for B. The zeolites SSZ-26 and SSZ-33, also of the CON structure type are described in U.S. Pat. No. 4,910,006 and U.S. Pat. No. 4,963,337 respectively. SSZ-33 is also described as a borosilicate. All 3 members of the CON structure type use very complicated, difficult to synthesize structure directing agents which make commercial utilization difficult. The known member of the DFO structure type is DAF-1 which is described as an aluminophosphate in Chem. Commun. 1993, 633-35 and in Chem. Mater. 1999, 11, 158-63. Zeolites from the IWR and IWW structure types are synthesized only in hydrofluoric acid containing synthesis routes, making commercial utilization difficult.

One particular zeolite of the MSE structure type, designated MCM-68, was disclosed by Calabro et al. in 1999 (U.S. Pat. No. 6,049,018). This patent describes the synthesis of MCM-68 from dication directing agents, N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication. MCM-68 was found to have at least one channel system in which each channel is defined by a 12-membered ring of tetrahedrally coordinated atoms and at least two further independent channel systems in which each channel is defined by a 10-membered ring of tetrahedrally coordinated atoms wherein the number of unique 10-membered ring channels is twice the number of 12-membered ring channels, see US 2009/318696.

Applicants have successfully prepared a new family of materials designated UZM-35. The topology of the main component of the materials is similar to that observed for MCM-68. The materials are prepared via the use of simple, commercially available structure directing agents, such as dimethyldipropylammonium hydroxide, in concert with small amounts of $K^+$ and $Na^+$ together using the Charge Density Mismatch Approach to zeolite synthesis as shown in U.S. Pat. No. 7,578,993.

The UZM-35 family of materials is able to provide and maintain high conversion during xylene and ethylbenzene isomerization reactions and minimize ring loss. This is believed to be due to its particular pore geometry and framework Si/Al mole ratio. The UZM-35 zeolitic composition contains significant amounts of Al in the tetrahedral framework, with the mole ratio of Si/Al ranging from about 2 to about 12. The Al content in the framework is known to provide acid sites required for high activity in isomerization processes.

Due to the unique structure of UZM-35, catalysts made from UZM-35 are able to show an advantage of about 30 to about 40% in ring retention over 12-membered ring channel MTW zeolite catalyst in proof of principle testing. Furthermore, a UZM-35 containing extrudate also shows a different distribution of aromatic by-products and unique character during initial line-out period as compared to MTW zeolite-containing extrudates. Specifically, the by-product yields diminish without any decrease in xylene isomerization activity, suggesting fouling of sites specific to undesired reactions.

SUMMARY OF THE INVENTION

The present invention relates to a process of xylenes and ethylbenzene isomerization using a catalyst comprising UZM-35 composition. The process comprises contacting the xylenes and ethylbenzene with the UZM-35 zeolitic composition at isomerization conditions to give a catalytically isomerized product. Isomerization conditions typically comprise a temperature of about 100° to about 500° C., a pressure of about 10 kPa to about 5 MPa absolute, a liquid hourly space velocity from about 0.5 to 10 hr$^{-1}$ and a hydrogen-to-hydrocarbon mole ratio from about 0.5:1 to 10:1.

The UZM-35 composition is a microporous crystalline zeolite composition having a three-dimensional framework of at least $AlO_2$ and $SiO_2$ tetrahedral units and an empirical composition in the as synthesized and anhydrous basis expressed by an empirical formula of:

$$M_m^+ R_r^+ Al_{1-x} E_x Si_y O_z$$

where M represents a combination of potassium and sodium exchangeable cations, "m" is the mole ratio of M to (Al+E) and varies from about 0.05 to about 3, R is a singly charged organoammonium cation selected from the group consisting of dimethyldipropylammonium (DMDPA$^+$), dimethyldiisopropylammonium (DMDIP$^+$), choline, ethyltrimethylammonium (ETMA$^+$), diethyldimethylammonium (DEDMA$^+$), trimethylpropylammonium, trimethylbutylammonium, dimethyldiethanolammonium, tetraethylammonium (TEA$^+$), tetrapropylammonium (TPA$^+$), methyltripropylammonium, and mixtures thereof, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of 0 to (Al+E) and has a value determined by the equation:

$$z=(m+r+3+4\cdot y)/2$$

and is characterized in that it has the x-ray diffraction pattern having at least the d-spacings and intensities set forth in Table A:

TABLE A

| 2θ | d (Å) | I/I$_O$% |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w | and is thermally stable up to a temperature of greater than 400° C. in one embodiment and 600° C. in another embodiment. When using a the Rietveld refinement method described in J. Appl. Cryst. (1969) 2, 65-71) the x-ray diffraction pattern has at least the d-spacings and intensities set forth in Table A'

TABLE A'

| 2θ | d (Å) | I/I$_O$% |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

The crystalline microporous zeolite composition described above may be synthesized by forming a reaction mixture containing reactive sources of M, R, Al, Si and optionally E and heating the reaction mixture at a temperature of about 150° C. to about 200° C., or about 165° C. to about 185° C., for a time sufficient to form the zeolite composition, the reaction mixture having a composition expressed in terms of mole ratios of the oxides of:

$$aM_2O : bR_{2/p}O : 1-cAl_2O_3 : cE_2O_3 : dSiO_2 : eH_2O$$

where "a" has a value of about 0.05 to about 1.25, "b" has a value of about 1.5 to about 40, "p" is the weighted average valance of R and varies from 1 to about 2, "c" has a value of 0 to about 1.0, "d" has a value of about 4 to about 40, "e" has a value of about 25 to about 4000.

DETAILED DESCRIPTION OF THE INVENTION

Figure 1:
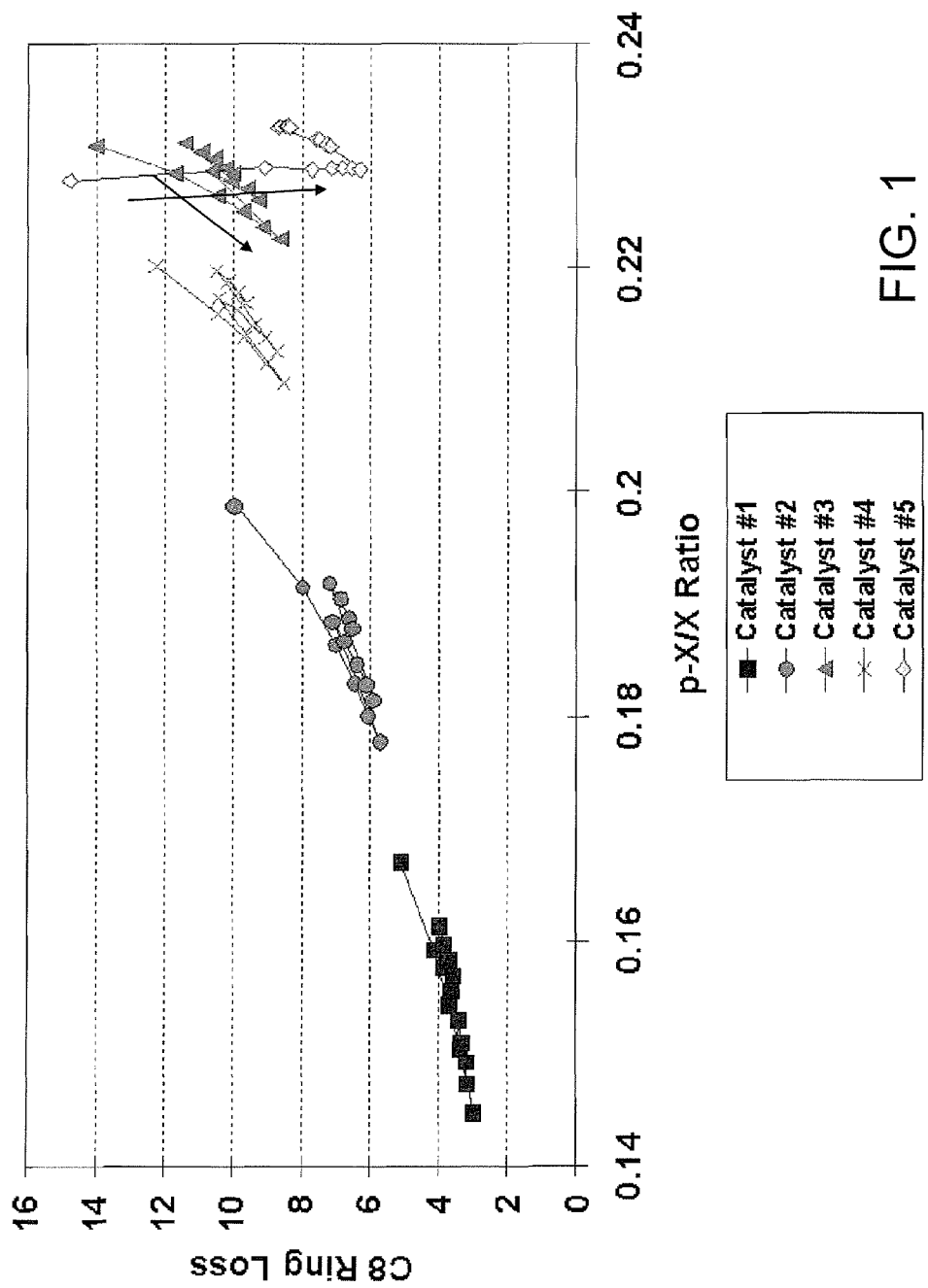
FIG. 1 is a plot of the results for each experiment, where the y-axis is $C_8$ ring loss, and the x-axis is the ratio of the amount of para-xylene to the amount of total xylene (PX:X). The "$C_8$ ring loss" is in units of mol-% defined as (1−($C_8$ naphthenes and aromatics in produce)/$C_8$ naphthenes and aromatics in feed))*100.

Applicants have prepared an aluminosilicate zeolitic UZM-35 composition which has a main component whose topological structure is related to MSE as described in *Atlas of Zeolite Framework Types*, which is maintained by the International Zeolite Association Structure Commission at http://www.iza-structure.org/databases/. As is shown in U.S. Ser. No. 12/241,302 in detail, UZM-35 composition is different from MCM-68 in a number of its characteristics. The instant microporous crystalline zeolitic UZM-35 composition, has an empirical composition in the as-synthesized form and on an anhydrous basis expressed by the empirical formula:

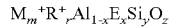

where M represents a combination of potassium and sodium exchangeable cations. R is a singly charged organoammonium cation, examples of which include but are not limited to the dimethyldipropylammonium cation (DMDPA$^+$), dimethyldiisopropylammonium (DMDIP$^+$), choline [(CH$_3$)$_3$N(CH$_2$)$_2$OH]$^+$, ETMA$^+$, DEDMA$^+$, trimethylpropylammonium, trimethylbutylammonium, dimethyldiethanolammonium, methyltripropylammonium, TEA$^+$, TPA$^+$ and mixtures thereof and "r" is the mole ratio of R to (Al+E) and varies from about 0.25 to about 2.0 while "m" is the mole ratio of M to (Al+E) and varies from about 0.05 to about 3. The mole ratio of silicon to (Al+E) is represented by "y" which varies from about 2 to about 30. E is an element which is tetrahedrally coordinated, is present in the framework and is selected from the group consisting of gallium, iron and boron. The mole fraction of E is represented by "x" and has a value from 0 to about 1.0, while "z" is the mole ratio of 0 to (Al+E) and is given by the equation:

$$z=(m·n+r+3+4·y)/2.$$

Where M is only one metal, then the weighted average valence is the valence of that one metal, i.e. +1 or +2. However, when more than one M metal is present, the total amount of:

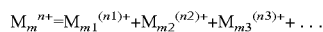

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

The microporous crystalline zeolitic UZM-35 composition, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of dimethyldipropylammonium, choline, ETMA, DEDMA, TEA, TPA, trimethylpropylammonium, trimethylbutylammonium, dimethyldiethanolammonium and mixtures thereof, and the sources include the hydroxide, chloride, bromide, iodide and fluoride compounds. Specific examples include without limitation dimethyldipropylammonium hydroxide, dimethyldipropylammonium chloride, dimethyldipropylammonium bromide, dimethyldiisopropylammonium hydroxide, dimethyldiisopropylammonium chloride, dimethyldiisopropylammonium bromide, ethyltrimethylammonium hydroxide, diethyldimethylammonium hydroxide, tetraethylammonium hydroxide, tetrapropylammonium hydroxide, and tetrapropylammonium chloride.

Note that during synthesis, the metal M is +1 valance, specifically potassium and sodium. However, in an alternative embodiment, the composition may undergo additional ion exchange steps post synthesis to provide a material with one or more metals, M, having a +2 valance.

The reaction mixture containing reactive sources of the desired components can be described in terms of molar ratios of the oxides by the formula:

where "a" varies from about 0.05 to about 1.25, "b" varies from about 1.5 to about 40, "c" varies from 0 to 1.0, "d" varies from about 4 to about 40, "e" varies from about 25 to about 4000, and "p" is the weighted average valence of R and varies from 1 to about 2. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-35 seeds can optionally be added to the reaction mixture in order to accelerate the formation of the zeolite.

A preferred synthetic approach to make UZM-35 composition utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-35 seeds have been generated using this approach, the seeds can be used in a single step synthesis of UZM-35, using, for example, a combination of dimethyldipropylammonium hydroxide and the alkali cations. The use of commercially available dimethyldipropylammonium hydroxide to prepare UZM-35 offers a great economic advantage over the structure directing agents previously employed (N,N,N',N'-tetraalkylbicyclo[2.2.2]oct-7-ene-2R,3S:5R,6S-dipyrrolidinium dication, N,N,N',N'-tetraalkylbicyclo[2.2.2] octane-2R,3S:5R,6S-dipyrrolidinium dication, and 1,1-dimethyl-4-cyclohexylpiperazinium cation) to prepare aluminosilicates with the MSE topology. Additionally, dimethyldipropyl ammonium hydroxide can be employed as the hydroxide or the chloride in concert with other inexpensive organoammonium hydroxides using the charge density mismatch concept to reduce costs even further.

The UZM-35 aluminosilicate zeolitic composition, which is obtained from the above-described process, is characterized by the x-ray diffraction pattern, having at least the d-spacings and relative intensities set forth in Table A below.

TABLE A

| 2θ | d (Å) | I/I$_O$ % |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w |

As will be shown in detail in the examples, the UZM-35 material is thermally and catalytically stable up to a temperature of at least 400° C. and in another embodiment, up to about 600° C. The UZM-35 composition as synthesized comprises a MSE topology zeolite, a MFI topology zeolite and an ERI topology zeolite. Typically, the amount of MSE zeolite in the composition will vary from about 55 wt % to about 75 wt. % or from about 55 wt-% to about 90 wt.-%. The amount of MFI zeolite varies from about 20 wt-% to about 35 wt-% of the composition or from about 10 wt-% to about 35 wt.-%, and the amount of ERI zeolite varies from about 3 wt-% to about 9 wt-% of the composition or from about 3 wt-% to about 10 wt.-%. Of course, the sum of the amount of the three zeolites, absent any other impurities, adds up to 100 wt % of the composition. When using a the Rietveld refinement method described in J. Appl. Cryst. (1969) 2, 65-71) the x-ray diffraction pattern has at least the d-spacings and intensities set forth in Table A'

TABLE A'

| 2θ | d (Å) | I/I$_O$ % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

One advantage of the UZM-35 material is that it may be used as a xylene and ethylbenzene isomerization catalyst without having to remove the potassium from the as synthesized material. In other words, the potassium does not need to be removed in order for the isomerization catalyst to be active. The catalyst, in its catalytically active state, may contain molar ratios of potassium to aluminum of less than 0.90.

As synthesized, the UZM-35 material will contain some of the exchangeable or charge balancing cations in its pores. These exchangeable cations can be exchanged for other cations, or in the case of organic cations, they can be removed by heating under controlled conditions. Because UZM-35 contains a large pore zeolite, it is also possible to remove some organic cations directly by ion exchange. The UZM-35 zeolitic composition may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al ratio, acidity, thermal stability, and the like.

The UZM-35 composition preferably is mixed with a binder for convenient formation of catalyst particles in a proportion of about 1 to 100 mass % zeolite and 0 to 99 mass-% binder, with the composition preferably comprising from about 2 to 90 mass-% of the composite. The binder should preferably be porous, have a surface area of about 5 to about 800 m$^2$/g, and relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, silica, silica gel, and clays. Preferred binders are amorphous silica and alumina, including gamma-, eta-, and theta-alumina, with gamma- and eta-alumina being especially preferred.

The UZM-35 composition with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. and subjected to a calcination procedure at a temperature of about 450-700° C. for a period of about 1 to about 20 hours. This treatment effects conversion of the hydrogel to the corresponding alumina matrix.

Catalysts of the invention comprise a hydrogenation catalyst component, which is a platinum-group metal, including one or more of platinum, palladium, rhodium, ruthenium, osmium, and iridium. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 5 mass-% and preferably from about 0.1 to about 2% of the final catalyst composite, calculated on an elemental basis.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the zeolite and binder. Yet another method of effecting a suitable metal distribution is by compositing the metal component with the binder prior to co-extruding the zeolite and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst composite of the present invention may contain a halogen component. The halogen component may be either fluorine, chlorine, bromine or iodine or mixtures thereof, with chlorine being preferred. The halogen component is generally present in a combined state with the inorganic-oxide support. The optional halogen component is preferably well dispersed throughout the catalyst and may comprise from more than 0.2 to about 5 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and, usually, calcined at a temperature of from 400° to about 650° C. in an air atmosphere for a period of from about 1 to about 10 hours until the metallic compounds present are converted substantially to the oxide form. If desired, the optional halogen component may be adjusted by including a halogen or halogen-containing compound in the air atmosphere.

The resultant calcined composite optimally is subjected to a substantially water-free reduction step to insure a uniform and finely divided dispersion of the optional metallic components. The reduction optionally may be effected in situ. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

The feedstock to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include without limitation ortho-xylene, meta-xylene, para-xylene, ethylbenzene, ethyltoluenes, tri-methylbenzenes, di-ethylbenzenes, tri-ethyl-benzenes, methylpropylbenzenes, ethylpropylbenzenes, di-isopropylbenzenes, and mixtures thereof.

Isomerization of a $C_8$-aromatic mixture containing ethylbenzene and xylenes is a particularly preferred application for the zeolites of the invention. Generally such mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially (defined herein as a difference of at least 5 mass-% of the total $C_8$ aromatics) from the thermodynamic equilibrium concentration of that isomer at isomerization conditions. Usually the non-equilibrium mixture is prepared by removal of para- and/or ortho-xylene from a fresh $C_8$ aromatic mixture obtained from an aromatics-production process, and preferably the non-equilibrium mixture contains less than 5 mass-% para-xylene.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a UZM-35 containing catalyst described herein in an alkylaromatic hydrocarbon isomerization zone. Contacting may be effected using the catalyst in a fixed-bed system, a moving-bed system, a fluidized-bed system, or in a batch-type operation. In a fixed-bed system, the danger of attrition loss of the valuable catalyst may be minimized and operation is simplified. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 0° to 600° C. or more, with a specific embodiment in the range of from about 100° to 500° C. The pressure generally is from about 10 kPa to about 5 MPa absolute, with one embodiment being less than about 5 MPa absolute. Sufficient catalyst is contained in the isomerization zone to provide a liquid hourly space velocity with respect to the hydrocarbon feed mixture of from about 0.1 to 30 $hr^{-1}$, with a specific embodiment of 0.5 to 10 $hr^{-1}$. The hydrocarbon feed mixture optimally is reacted in admixture with hydrogen at a hydrogen/hydrocarbon mole ratio of about 0.5:1 to about 10:1 or more. Other inert diluents such as nitrogen, argon and light hydrocarbons may be present.

The reaction proceeds via the mechanism of isomerizing xylenes while reacting ethylbenzene to form a xylene mixture via conversion to and reconversion from naphthenes. The yield of xylenes in the product thus is enhanced by forming xylenes from ethylbenzene. The loss of $C_8$ aromatics through the reaction thus is desirably low.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, each incorporated herein by reference.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The following examples are presented in illustration of this invention and are not intended as undue limitations on the generally broad scope of the invention as set out in the appended claims.

The structure of the UZM-35 zeolitic composition of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate reaction solution was prepared by first mixing 27.17 g of aluminum hydroxide (27.78 mass-% Al) and 1053.58 g dimethyldipropylammonium hydroxide (18.8 mass-% solution), while stirring vigorously. After thorough mixing, 505.96 g Ludox™ AS-40 (40 mass-% $SiO_2$) was added. The reaction mixture was homogenized for an additional hour with a high speed mechanical stirrer, sealed in a Teflon bottle, and placed in an oven overnight at 100° C. Analysis showed the aluminosilicate solution contained 6.16 wt. % Si and 0.67 wt. % Al (Si/Al molar ratio of 8.83).

A 1200 g portion of the above aluminosilicate solution was continuously stirred. A composite aqueous solution containing 28.56 g of KOH and 3.6 g of NaOH dissolved in 150 g distilled water, was added, drop-wise, to the aluminosilicate solution. After the addition was completed, the resulting reaction mixture was homogenized for 1 hour, transferred to a 2000 ml Parr stainless steel autoclave which was heated to 175° C. and maintained at that temperature for 216 hrs.

The solid product was recovered by centrifugation, washed with de-ionized water and dried at 95° C. to 100° C. The product was identified as UZM-35 by xrd. Representative diffraction lines observed for the product are shown in Table 1. The product composition was determined by elemental analysis to consist of the following mole ratios: Si/Al=7.92, Na/Al=0.1, K/Al=0.48.

TABLE 1

| 2θ | d (Å) | $I/I_O$ % |
|---|---|---|
| 6.65 | 13.26 | m |
| 6.95 | 12.69 | m |
| 8.10 | 10.90 | m |

TABLE 1-continued

| 2θ | d (Å) | $I/I_O$ % |
|---|---|---|
| 8.87 | 9.95 | m |
| 9.76 | 9.05 | m |
| 10.83 | 8.13 | w |
| 13.76 | 6.43 | w |
| 15.22 | 5.81 | w |
| 18.00 | 4.92 | w |
| 19.46 | 4.55 | m |
| 19.62 | 4.52 | m |
| 20.06 | 4.42 | m |
| 20.63 | 4.3 | m |
| 21.1 | 4.20 | m |
| 21.76 | 4.08 | vs |
| 21.92 | 4.05 | m |
| 22.07 | 4.03 | m |
| 22.55 | 3.93 | m |
| 22.73 | 3.90 | m |
| 23.08 | 3.85 | s |
| 23.42 | 3.79 | m |
| 23.51 | 3.77 | m |
| 24.04 | 3.69 | m |
| 24.53 | 3.62 | w |
| 25.9 | 3.43 | m |
| 25.99 | 3.42 | w |
| 26.27 | 3.38 | m |
| 26.92 | 3.3 | m |
| 27.57 | 3.23 | m |
| 27.76 | 3.21 | m |
| 28.17 | 3.16 | m |
| 28.86 | 3.09 | w |
| 29.27 | 3.04 | m |
| 29.72 | 3.00 | w |
| 30.26 | 2.95 | w |
| 30.91 | 2.88 | m |
| 31.38 | 2.84 | w |
| 33.61 | 2.68 | w |
| 34.65 | 2.58 | w |
| 35.43 | 2.53 | w |
| 36.18 | 2.48 | w |
| 41.77 | 2.16 | w |
| 44.7 | 2.02 | w |
| 45.32 | 1.99 | w |
| 45.63 | 1.98 | w |
| 46.55 | 1.94 | w |
| 47.62 | 1.90 | w |
| 47.94 | 1.89 | w |
| 49.70 | 1.83 | w |
| 51.06 | 1.78 | w |

EXAMPLE 2

The UZM-35 of Example 1 was calcined at 570° C. for 7 hours under nitrogen and then under air. The UZM-35 was then ammonium ion exchanged to exchange $Na^+$ or $K^+$ cations for $NH_4^+$. The UZM-35 was ammonium ion-exchanged by contacting 500 mL of 1 M $NH_4NO_3$ solution with 40 g UZM-35 at 80° C. and stirring for 1 hour, filtered and washed. The procedure was repeated three times. The ion-exchanged UZM-35 was then calcined at 550° C. in air for 2 h to convert $NH_4^+$ to $H^+$ by loss of ammonia.

EXAMPLE 3

Alternatively, the ammonium exchange was performed first and then followed by calcination to remove the template and exchange $Na^+$ or $K^+$ cations for $NH_4^+$. The UZM-35 of Example 1 was ammonium ion exchanged by contacting 1000 mL of 1 M $NH_4NO_3$ solution with 100 g UZM-35 at 80° C. and stirring for 2 hours. The ion-exchanged UZM-35 was then calcined at 560° C. for 7 hours under nitrogen and then air. A second ion-exchange was carried out by contacting 1000 mL of 1 M NH₄NO₃ solution with 95 g UZM-35 at 80° C. and stirring for 1 hour. The ion-exchanged UZM-35 was filtered and dried.

EXAMPLE 4

The UZM-35 of Example 3 was then steamed at 600° C. for 2 h in a vertical steamer by passing an air stream containing 50 vol-% steam over the UZM-35. The steamed UZM-35 was ion-exchanged with the NH₄NO₃ solution again. The resulting steam-ammonium UZM-35 was extruded at 70/30 ratio with alumina. The extrudates were calcined at 550° C. in air for 2 hours to convert NH₄⁺ to H⁺ by loss of ammonia.

COMPARATIVE EXAMPLE 5

Three different catalysts were compared with an embodiment of the claimed catalyst for performance in xylene isomerization. The first and second catalysts were extrudates made with 20 Si/Al mole ratio MTW zeolite powder made according to the method described in U.S. Pat. No. 7,525,008 and V-251 alumina (available from UOP, LLC). The first catalyst had a 20 weight-% zeolite concentration, while the second catalyst had a 50 weight-% zeolite concentration, based on the weight of the extrudate.

The third and fourth catalysts were made with 20 Si/Al mole ratio MTW zeolite and both had 80 wt.-% zeolite concentrations based on the catalytic composite, with an alumina binder. The third catalyst was an oil-dropped sphere and the fourth catalyst was an extrudate which had been ion exchanged with ammonium nitrate, washed, and calcined.

The embodiment of the invention tested as the fifth catalyst was a steamed 70 weight-% UZM-35 zeolitic composition extrudate having an alumina binder.

In each experiment, about 2 grams of catalyst was loaded into a fixed bed reactor. Feed and hydrogen were introduced to the reactor to contact the catalyst. The feed was a mixture of 56 weight-% meta-xylene, 22 weight-% ortho-xylene, 1 weight-% para-xylene, 1 weight-% toluene, and 6 weight-% C8 naphthenes with the balance ethylbenzene. The feed was pumped at 10 WHSV, and the H₂/HC ratio was 4. The reactor was operated at about 786 kPa absolute and each catalyst was tested at temperatures 365° C., 375° C. and 385° C. The effluent of the reactor was monitored using gas chromatography. For each experiment, the results were plotted as shown in FIG. 1 where the y-axis is C₈ ring loss, and the x-axis is the ratio of the amount of para-xylene to the amount of total xylene (PX:X). The "C₈ ring loss" is in units of mol-% defined as (1−(C₈ naphthenes and aromatics in produce)/C₈ naphthenes and aromatics in feed))*100.

Figure 2:
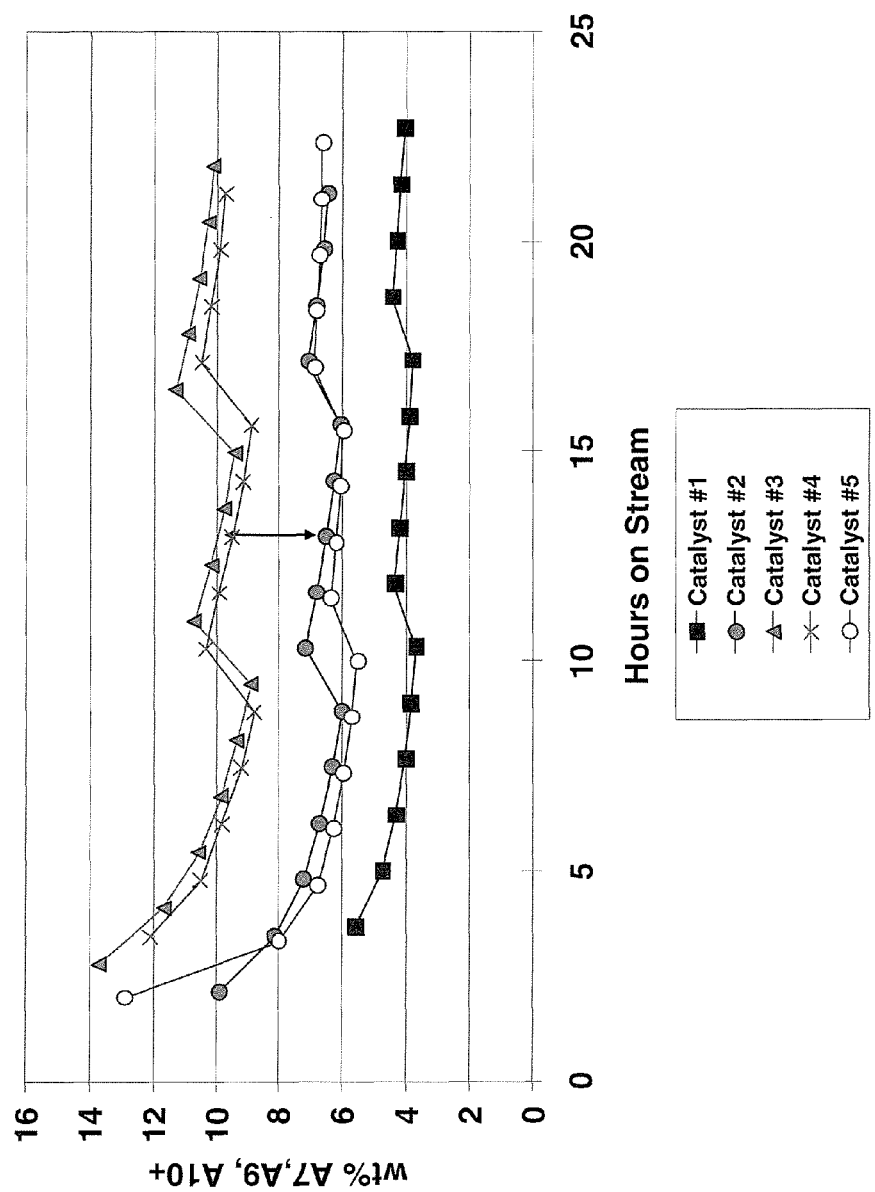
FIG. 2 is a plot of wt-% A7, A9 and A10+ versus hours on stream for each of the experiments demonstrating that the ring loss that is present in mostly transalkylation.
Figure 3:
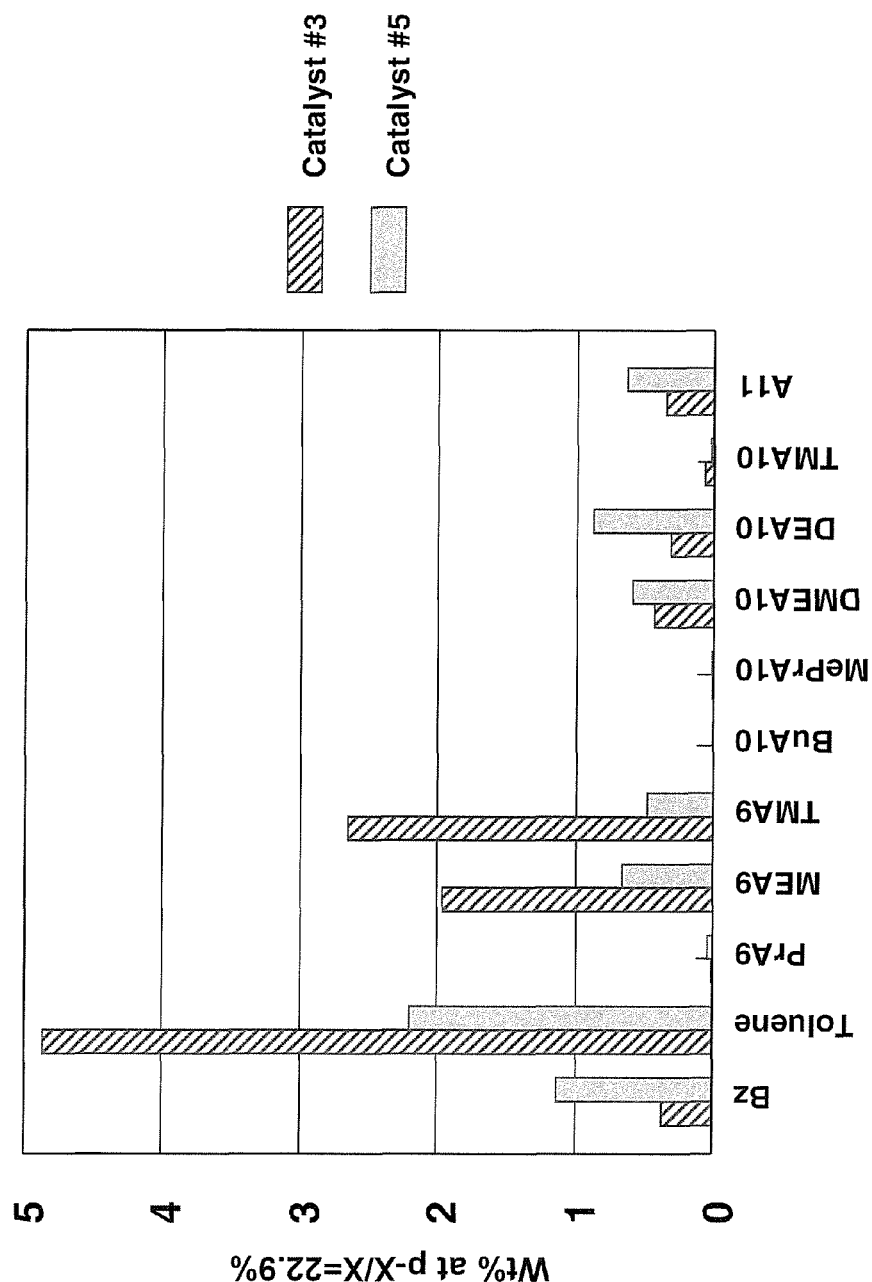
FIG. 3 shows the product distribution resulting from using catalyst #3 and catalyst #5 of the examples.
Figure 4:
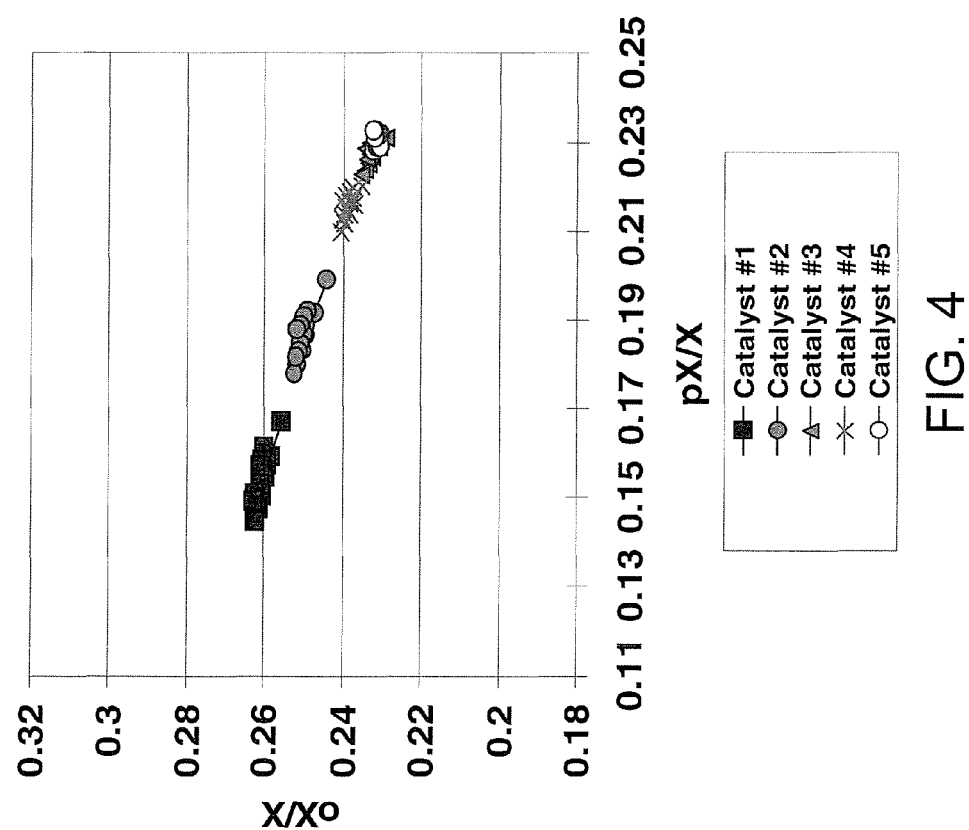
FIG. 4 shows that the catalyst of the invention provides xylenes on the same ortho-xylene versus para-xylene curve as MTW zeolite catalysts.

As FIG. 1 shows, the embodiment of the invention demonstrated an interesting trend with time on stream. The selectivity of the catalyst of the invention improves early in the run without significant loss of xylene isomerization activity, thereby providing an initial reduction in byproducts. Also, the catalyst of the invention provided an advantage in lower ring loss as compared to the oil dropped sphere of 80-wt. % MTW with alumina binder. The ring loss that is present is mostly transalkylation, see FIG. 2 where the comparison of Catalyst #5 to Catalyst #3 shows its lower ring loss at equivalent P−X/X. The catalyst of the invention has a different product distribution than MTW zeolite, resulting in a different distribution, see FIG. 3, which shows the product distribution in weight-percent at P−X/X of 22.9 weight-%. Consistent with MTW zeolite, there is no restriction of ortho-xylene, see FIG. 4 which shows that the catalyst of the invention provides xylenes on the same ortho-xylene versus para-xylene curve as MTW zeolite.

COMPARATIVE EXAMPLE 6

Three different catalysts were compared with an embodiment of the claimed catalyst for performance in xylene transalkylation. The first catalyst was an extrudate of UZM-35 composition powder and V-251 alumina where the first catalyst has a 70 weight-% zeolite concentration based on the finished extrudate. The second catalyst was an extrudate of a 2.2 wt. % Ga and 0.6 wt. % Al on MFI zeolite with V-251 alumina binder in accordance with the teachings of U.S. Pat. No. 4,957,891. The second catalyst had a 50 weight-% zeolite concentration, based on the weight of the extrudate. The third catalyst was an ammonium nitrate-exchanged, steamed oil-dropped sphere of 65 weight percent MFI and an aluminophosphate binder prepared using the method of Example 1 of U.S. Pat. No. 6,143,941.

In each experiment, about 1 gram of catalyst was loaded into a fixed bed reactor. Feed and hydrogen were introduced to the reactor to contact the catalyst. The feed was a mixture of 60 weight-% meta-xylene, 25 weight-% ortho-xylene, 15 weight-% ethylbenzene. The feed was pumped at 10 WHSV based on the amount of zeolite, and the H₂/HC ratio was 4. The reactor was operated at about 786 kPa absolute and each catalyst was tested at temperatures 375° C., 385° C. and 395° C. The catalysts were introduced as a physical mixture with 0.4 grams of 14/20 meshed 0.3 weight-% platinum on alumina catalyst modified with 0.6 weight-% indium and 0.3 weight-% tin in accordance with Example III in U.S. Pat. No. 6,048,449.

The effluent of the reactor was monitored using gas chromatography. For each experiment, the results are shown in Table 2. From Table 2 it can be seen that the conversion of ethylbenzene is relatively low compared to the MFI zeolite structure. Much of the conversion is ethyl transfer to other aromatics. The xylene isomerization activity is high as shown by the ratio of para-xylene to total xylenes, and is close to equilibrium.

TABLE 2

| To Achieve 60% ethylbenzene conversion | Catalyst #1 | Catalyst #2 | Catalyst #3 |
|---|---|---|---|
| Temp ° C. | 396 | 375 | 365 |
| Net wt % toluene and trimethyl-benzenes. | 8.1 | 2.8 | 2.5 |
| Para-xylene: Xylene ratio | 0.239 | 0.241 | 0.230 |

EXAMPLE 7

An aluminosilicate reaction solution was prepared by first mixing 86.33 g of aluminum hydroxide (26.97 mass-% Al) and 1437.67 g of dimethyldipropylammonium hydroxide (40.66 mass-% solution), while stirring vigorously. After thorough mixing, 1366.88 g Ludox™ AS-40 (SiO₂, mass-40%) was added. The reaction mixture was homogenized for 20 minutes with a high-speed mechanical stirrer, the aluminosilicate colloidal solution was continuously stirred and an aqueous solution containing 83.04 g of KOH and 17.38 g of NaOH dissolved in 808.7 g H₂O, was added, drop wise, to the aluminosilicate solution. After the addition was completed, the resulting reaction mixture was homogenized for ½ hour, transferred to (3) 2000 ml Parr stainless steel autoclave which were heated to 175° C. and maintained at that temperature for 9 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 72.1 wt-% MSE type zeolite with a lattice parameter of 18.372 angstroms for a and 20.285 angstroms for c; 24.1 wt-% MFI zeolite with a lattice parameter of 20.101 angstroms for a, 19.862 angstroms for b and 13.402 for c, and 3.7 wt-% ERI zeolite with a lattice parameter of 13.222 angstroms for a and 14.900 angstroms for c. Chemical analysis gave a product composition of mole ratio Si/Al 8.9. BET Surface area was determined to be 408 m2/g and micropore volume was 0.197 cc/g. Representative diffraction lines observed for the product are shown in Table 3.

TABLE 3

| 2θ | d (Å) | I/I$_O$ % |
|---|---|---|
| 6.5 | 13.58 | m |
| 6.8 | 12.99 | s |
| 7.79 | 11.32 | m |
| 8.07 | 10.93 | m |
| 8.719 | 10.13 | m |
| 9.63 | 9.17 | s |
| 10.75 | 8.21 | w |
| 13.63 | 6.49 | w |
| 14.74 | 6.00 | w |
| 15.56 | 5.69 | w |
| 15.86 | 5.58 | w |
| 19.46 | 4.55 | m |
| 19.899 | 4.45 | m |
| 20.518 | 4.32 | m |
| 20.94 | 4.23 | w |
| 21.618 | 4.1 | vs |
| 21.799 | 4.07 | s |
| 22.399 | 3.96 | m |
| 22.93 | 3.87 | s |
| 23.299 | 3.81 | m |
| 23.78 | 3.73 | m |
| 24.82 | 3.58 | w |
| 25.76 | 3.45 | w |
| 26.09 | 3.41 | m |
| 26.74 | 3.33 | m |
| 27.42 | 3.24 | m |
| 28.04 | 3.17 | w |
| 29.10 | 3.06 | w |
| 29.54 | 3.02 | w |
| 29.75 | 2.99 | w |
| 30.13 | 2.96 | m |
| 30.73 | 2.9 | m |
| 31.47 | 2.83 | w |
| 33.19 | 2.69 | w |
| 34.46 | 2.6 | w |
| 35.18 | 2.54 | w |
| 35.59 | 2.51 | w |
| 36.04 | 2.49 | w |
| 41.65 | 2.16 | w |
| 44.57 | 2.03 | w |
| 47.48 | 1.91 | w |
| 49.53 | 1.83 | w |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a mixture of 64.4 wt % MSE zeolite with a lattice parameter of 18.371 angstroms for a and 20.235 angstroms for c; 30.7 wt % MFI zeolite with a lattice parameter of 20.048 angstroms for a, 19.880 angstroms for b and 13.403 angstroms for c, and 4.8 wt % ERI zeolite with a lattice parameter of 13.071 angstroms for a and 15.238 angstroms for c. A 160 g portion of the calcined UZM-35 sample (Si/Al mole ratio 8.9) was NH4 exchanged. A solution was prepared by dissolving 160 g of NH$_4$NO$_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs. Elemental analyses of this sample shows a Si/Al mole ratio to Si/Al=9.07, Na/Al=0.01, K/Al=0.11. Representative diffraction lines observed for the product are shown in Table 4.

TABLE 4

| 2θ | d (Å) | I/I$_O$ % |
|---|---|---|
| 6.67 | 13.22 | m |
| 6.97 | 12.65 | m-s |
| 7.94 | 11.12 | m |
| 8.14 | 10.85 | m |
| 8.93 | 9.88 | m |
| 9.79 | 9.01 | m-s |
| 10.92 | 8.09 | m |
| 13.78 | 6.42 | w |
| 14.1 | 6.27 | w |
| 14.97 | 5.91 | w |
| 15.7 | 5.63 | w |
| 16.05 | 5.51 | w |
| 17.57 | 5.04 | w |
| 19.64 | 4.51 | m |
| 20.05 | 4.42 | m |
| 20.65 | 4.29 | m |
| 21.13 | 4.19 | w |
| 21.77 | 4.07 | vs |
| 21.98 | 4.04 | s-vs |
| 22.62 | 3.92 | s |
| 23.14 | 3.84 | vs |
| 23.46 | 3.78 | m |
| 23.94 | 3.71 | m |
| 24.58 | 3.61 | w |
| 24.83 | 3.58 | w |
| 25.2 | 3.53 | m |
| 25.92 | 3.43 | w |
| 26.24 | 3.39 | m |
| 26.52 | 3.35 | m |
| 26.96 | 3.3 | m |
| 27.6 | 3.22 | m-s |
| 28.25 | 3.15 | m |
| 28.79 | 3.09 | m |
| 29.3 | 3.04 | m |
| 29.68 | 3 | w |
| 29.96 | 2.98 | m |
| 30.35 | 2.94 | m |
| 30.89 | 2.89 | m |
| 31.46 | 2.84 | m |
| 31.81 | 2.81 | m |
| 33.4 | 2.68 | m |
| 36.22 | 2.47 | w |
| 41.83 | 2.15 | w |
| 44.86 | 2.01 | w |
| 47.64 | 1.9 | w |
| 49.69 | 1.83 | w |

EXAMPLE 8

An aluminosilicate reaction solution was prepared by first mixing 29.01 g of aluminum hydroxide (26.97% Al) and 483.08 g of dimethyldipropylammonium hydroxide (40.66% solution), while stirring vigorously. After thorough mixing, 461.58 g Ludox™ AS-40 (SiO$_2$, 40%) was added. The reaction mixture was homogenized for 20 minutes with a high-speed mechanical stirrer, the aluminosilicate colloidal solution was continuously stirred and an aqueous solution containing 27.90 g of KOH and 3.46 g of NaOH dissolved in 269.98 g H$_2$O, was added, drop wise, to the aluminosilicate solution. After the addition was completed, the resulting reaction mixture was homogenized for ½ hour, transferred to a 2000 ml Parr stainless steel autoclave, which was heated to 175° C. and maintained at that temperature for 10 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 66.3 wt % MSE type zeolite with a lattice parameter of 18.369 angstroms for a and 20.284 angstroms for c; 25.5 wt % MFI with a lattice parameter of 20.136 angstroms for a, 19.976 angstroms for b and 13.443 angstroms for c, and 8.2 wt % ERI with a lattice parameter of 13.152 angstroms for a and 15.107 angstroms for c. Chemical analysis gave a product composition (mole ratio) of Si/Al=7.65, N/Al=0.38, K/Al=0.68, Na/Al=0.03. BET surface area was determined to be 404 m2/g and a micropore volume was 0.188 cc/g. Representative diffraction lines observed for the product are shown in Table 5.

TABLE 5

| $2\theta$ | d (Å) | $I/I_O$ % |
|---|---|---|
| 6.48 | 13.32 | 31.9 |
| 6.78 | 13.02 | 58.5 |
| 8.05 | 10.96 | 25.7 |
| 8.71 | 10.13 | 33.6 |
| 9.61 | 9.18 | 53.6 |
| 10.75 | 8.21 | 11.2 |
| 13.61 | 6.49 | 12.9 |
| 14.74 | 6 | 7.3 |
| 15.86 | 5.58 | 7.2 |
| 19.48 | 4.55 | 41.5 |
| 19.9 | 4.45 | 21.1 |
| 20.5 | 4.32 | 13.4 |
| 20.96 | 4.23 | 25.6 |
| 21.61 | 4.1 | 100 |
| 21.81 | 4.07 | 63.8 |
| 22.42 | 3.96 | 45.7 |
| 22.94 | 3.87 | 85.5 |
| 23.3 | 3.81 | 38.5 |
| 23.5 | 3.78 | 31.3 |
| 23.86 | 3.72 | 17.8 |
| 24.41 | 3.64 | 6.8 |
| 25.78 | 3.45 | 20.2 |
| 26.09 | 3.41 | 19.8 |
| 26.81 | 3.32 | 39.8 |
| 27.14 | 3.28 | 20.9 |
| 27.44 | 3.24 | 42.9 |
| 27.69 | 3.21 | 33 |
| 28.06 | 3.17 | 14.7 |
| 29.15 | 3.06 | 16.2 |
| 29.55 | 3.01 | 13.5 |
| 29.86 | 2.98 | 20.8 |
| 30.14 | 2.96 | 18.7 |
| 30.75 | 2.9 | 24.1 |
| 31.26 | 2.85 | 8.9 |
| 33.21 | 2.69 | 11.1 |
| 34.34 | 2.6 | 8.8 |
| 34.76 | 2.57 | 10.5 |
| 35.2 | 2.54 | 6.8 |
| 35.57 | 2.52 | 8.6 |
| 36.02 | 2.49 | 8 |
| 41.71 | 2.16 | 9.8 |
| 44.61 | 2.02 | 8.2 |
| 47.48 | 1.91 | 8 |
| 49.56 | 1.83 | 10.1 |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a UZM-35 composition of 61.9 wt-% MSE zeolite with a lattice parameter of 18.401 angstroms for a and 20.280 angstroms for c; 30.8 wt-% MFI zeolite with a lattice parameter of 20.114 angstroms for a, 19.919 angstroms for b and 13.432 angstroms for c, and 7.3-wt % ERI zeolite with a lattice parameter of 13.189 angstroms for a and 15.174 angstroms for c. A 100 g portion of the calcined UZM-35 sample (Si/Al mole ratio 7.65) was NH4 exchanged. A solution was prepared by dissolving 160 g of NH$_4$NO$_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs. Elemental analyses of this sample shows a Si/Al mole ratio to Si/Al=9.20, Na/Al=0.01, K/Al=0.10. Representative diffraction lines observed for the product are shown in Table 6.

TABLE 6

| $2\theta$ | d (Å) | $I/I_O$ % |
|---|---|---|
| 6.5 | 13.58 | m |
| 6.81 | 12.95 | m |
| 7.98 | 11.07 | m |
| 8.76 | 10.08 | m |
| 9.63 | 9.16 | m |
| 10.77 | 8.2 | m |
| 13.63 | 6.48 | m |
| 14.8 | 5.98 | w |
| 15.84 | 5.58 | w |
| 19.51 | 4.54 | m |
| 19.91 | 4.45 | m |
| 20.49 | 4.32 | m |
| 21.01 | 4.22 | m |
| 21.62 | 4.1 | vs |
| 22.49 | 3.94 | s |
| 23.02 | 3.86 | vs |
| 23.3 | 3.81 | m-s |
| 23.64 | 3.76 | m |
| 23.91 | 3.71 | m |
| 24.41 | 3.64 | m |
| 24.62 | 3.61 | w |
| 25.11 | 3.54 | w |
| 25.81 | 3.44 | m |
| 26.09 | 3.41 | m |
| 26.41 | 3.37 | m |
| 26.86 | 3.31 | m-s |
| 27.45 | 3.24 | m-s |
| 27.65 | 3.22 | m |
| 28.13 | 3.16 | m |
| 28.82 | 3.09 | w |
| 29.14 | 3.06 | m |
| 29.57 | 3.01 | w |
| 29.84 | 2.99 | m |
| 30.21 | 2.95 | m |
| 30.76 | 2.9 | m |
| 31.31 | 2.85 | w |
| 33.27 | 2.69 | w |
| 36.12 | 2.48 | w |
| 41.68 | 2.16 | w |
| 44.74 | 2.02 | w |
| 47.56 | 1.91 | w |
| 49.57 | 1.83 | w |

The invention claimed is:

1. A process for isomerizing a non-equilibrium feed mixture comprising xylenes and ethylbenzene comprising contacting the feed mixture in the presence of hydrogen in an isomerization zone with a catalyst at isomerization conditions and producing an isomerized product comprising a higher proportion of p-xylene than in the feed mixture, wherein the catalyst comprises a UZM-35 microporous crystalline zeolitic composition and a hydrogenation component, wherein the UZM-35 composition comprises at least a MSE type zeolite, a MFI type zeolite, and an ERI type zeolite, and has a three-dimensional framework of at least $AlO_2$ and $SiO_2$ tetrahedral units and an empirical composition in the as synthesized and anhydrous basis expressed by an empirical formula of:

$$M_m^{+}R_rAl_{1-x}E_xSi_yO_z$$

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is at least one element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A':

TABLE A'

| 2θ | d (Å) | I/I_O % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |

TABLE A'-continued

| 2θ | d (Å) | I/I_O % |
|---|---|---|
| 47.48-47.58 | 1.9-1.91 | w |
| 49.53-49.59 | 1.83-1.83 | w | and is thermally stable up to a temperature of at least 400° C.

2. The process of claim 1 further comprising recovery of ortho-xylene, para-xylene, or both from one or both of the isomerized product and fresh feed mixture.

3. The process of claim 1 where the isomerization conditions include a temperature of about 100° C. to about 500° C., a pressure from about 10 kPa absolute to about 5 MPa absolute atmospheres, a liquid hourly spare velocity of about 0.5 to about 10 hr$^{-1}$ and a hydrogen to hydrocarbon ratio of about 0.5:1 to about 10:1.

4. The process of claim 1 wherein "x" of the UZM-35 zeolitic composition is zero.

5. The process of claim 1 where R is a combination of dimethyldipropyl ammonium hydroxide and at least one singly charged organoammonium cation selected from the group consisting of TEA, TPA, ETMA, DEDMA, trimethylpropylammonium, dimethyldiisopropyl ammonium, trimethylbutylammonium, dimethyldiethanolammonium, and methyltripropylammonium.

6. The process of claim 1 wherein between about 1 and about 60 mass-% of the $C_8$ aromatics in the feed stream is ethylbenzene.

7. The process of claim 1 wherein the hydrogenation component comprises platinum group metal-containing component.

8. The process of claim 1 wherein the catalyst further comprises a metal modifier component or a halogen component.

9. The process of claim 1 wherein the UZM-35 composition comprises from about 55 wt % to about 90 wt. % of MSE zeolite.

10. The process of claim 1 wherein the UZM-35 composition comprises from about 10 wt-% to about 35 wt-% of MFI zeolite.

11. The process of claim 1 wherein the UZM-35 composition comprises and from about 3 wt-% to about 10 wt-% of ERI zeolite.

12. A process for isomerizing a non-equilibrium feed mixture comprising xylenes and ethylbenzene comprising contacting the feed mixture in the presence of hydrogen in an isomerization zone with a catalyst at isomerization conditions and producing an isomerized product comprising a lower proportion of ethylbenzene than in the feed mixture, wherein the catalyst comprises a UZM-35 microporous crystalline zeolitic composition and a hydrogenation component, wherein the UZM-35 composition comprises at least a MSE type zeolite, a MFI type zeolite, and an ERI type zeolite, and has a three-dimensional framework of at least $AlO_2$ and $SiO_2$ tetrahedral units and an empirical composition in the as synthesized and anhydrous basis expressed by an empirical formula of:

$$M_m^{+}R_rAl_{1-x}E_xSi_yO_z$$

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of 0 to (Al+E) and has a value determined by the equation:

$$z=(m+r+3+4\cdot y)/2$$

and is characterized in that it has the x-ray diffraction pattern having at least the d-spacing's and intensities set forth in Table A':

TABLE A'

| 2θ | d (Å) | I/I$_O$% |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

13. The process of claim 12 wherein "x" of the UZM-35 zeolitic composition is zero.

14. The process of claim 12 where R is a combination of dimethyldipropyl ammonium hydroxide and at least one singly charged organoammonium cation selected from the group consisting of TEA, TPA, ETMA, DEDMA, trimethylpropylammonium, dimethyldiisopropyl ammonium, trimethylbutylammonium, dimethyldiethanolammonium, and methyltripropylammonium.

15. The process of claim 12 where the isomerization conditions include a temperature of about 100° C. to about 500° C., a pressure from about 10 kPa absolute to about 5 MPa absolute atmospheres, a liquid hourly spare velocity of about 0.5 to about 10 hr$^{-1}$ and a hydrogen to hydrocarbon ratio of about 0.5:1 to about 10:1.

16. The process of claim 12 wherein between about 1 and about 60 mass-% of the C$_8$ aromatics in the feed stream is ethylbenzene.

17. The process of claim 12 wherein the hydrogenation component comprises platinum group metal-containing component, a metal modifier component, a halogen component, or combinations thereof.

18. The process of claim 12 wherein the UZM-35 composition comprises from about 55 wt % to about 90 wt. % of MSE zeolite.

19. The process of claim 12 wherein the UZM-35 composition comprises from about 10 wt-% to about 35 wt-% of MFI zeolite.

20. The process of claim 12 wherein the UZM-35 composition comprises from about 3 wt-% to about 10 wt-% of ERI zeolite.

* * * * *